(12) United States Patent
Cook

(10) Patent No.: US 6,290,667 B1
(45) Date of Patent: Sep. 18, 2001

(54) NASAL ASPIRATOR

(75) Inventor: Daniel G. Cook, Maple Plain, MN (US)

(73) Assignee: Health & Technology, Inc., Plymouth, MN (US)

( * ) Notice: Subject to any disclaimer, the term of this patent is extended or adjusted under 35 U.S.C. 154(b) by 0 days.

(21) Appl. No.: 09/329,879

(22) Filed: Jun. 11, 1999

(51) Int. Cl.[7] .................................................. A61N 1/30
(52) U.S. Cl. ........................ 604/19; 604/37; 604/98.02; 128/200.22
(58) Field of Search ................................ 604/19, 37, 54, 604/296, 298; 128/200.14, 200.22, 203.12, 203.28, 205.13, 205.14, 205.17; 222/72, 633, 92–96, 204, 527, 206–213, 528, 530, 542; 220/500, 501, 505, 323, 324, 354, 355, 720; D24/115; D9/529

(56) References Cited

U.S. PATENT DOCUMENTS

| | | | |
|---|---|---|---|
| 1,660,085 | * | 2/1928 | Nassau . |
| 2,511,469 | * | 6/1950 | Hawks ............................ 128/205.24 |
| 2,577,321 | * | 12/1951 | Filger . |
| 2,671,578 | * | 3/1954 | McBean . |
| 2,672,141 | * | 3/1954 | Filger . |
| 4,258,714 | * | 3/1981 | Leopoldi et al. ............... 128/203.12 |
| 4,564,129 | * | 1/1986 | Urban et al. ......................... 222/207 |
| 4,813,931 | * | 3/1989 | Hauze .................................... 604/54 |
| 5,062,835 | * | 11/1991 | Maitz et al. .................... 128/205.24 |
| 5,116,311 | * | 5/1992 | Lofstedt ................................ 604/54 |
| 5,643,202 | * | 7/1997 | Gravenstein et al. ................. 604/54 |
| 5,662,098 | * | 9/1997 | Yoshida .......................... 128/200.22 |
| 5,702,362 | * | 12/1997 | Herold et al. ......................... 604/58 |
| 5,894,967 | * | 4/1999 | Stahley et al. ....................... 222/633 |
| 5,921,233 | * | 7/1999 | Gold et al. ...................... 128/200.22 |

* cited by examiner

Primary Examiner—John G. Weiss
Assistant Examiner—Teena Mitchell
(74) Attorney, Agent, or Firm—Kinney & Lange, P.A.

(57) ABSTRACT

A nasal aspirator having a stem, a tip and a bulb. The stem having an inner lumen from a top to a bottom. The tip comprising of an aperture at a point that arches from a base, wherein the base is secured to the top of the stem. The bulb having a ribbed opening into an inner hollow cavity. The bottom of the stem being inserted through the ribbed opening and into the inner hollow cavity so that the top of the stem is secured at the ribbed opening of the bulb.

13 Claims, 1 Drawing Sheet

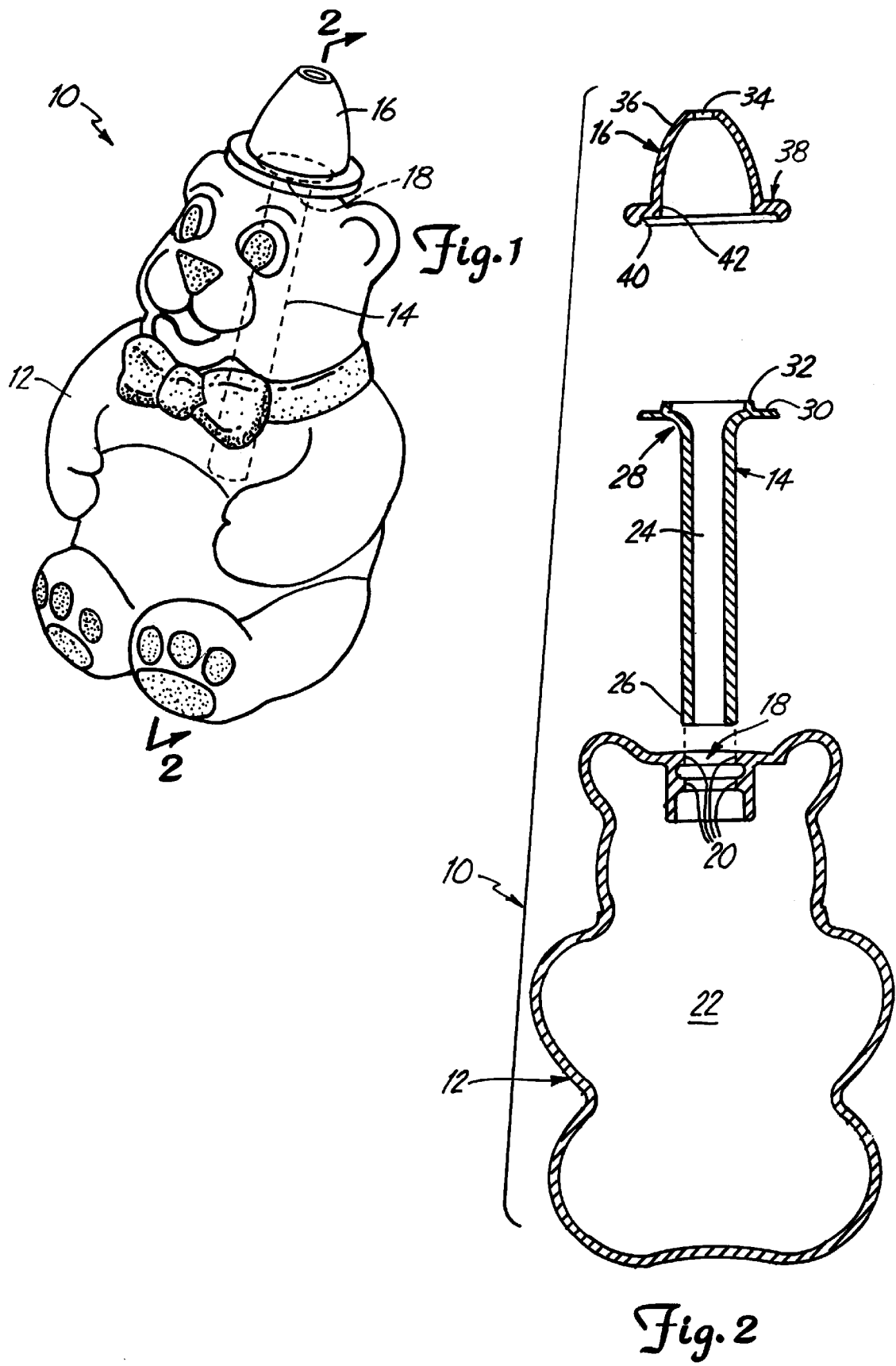

NASAL ASPIRATOR

BACKGROUND OF THE INVENTION

The invention relates to a nasal aspirator. More particularly, the invention relates to a nasal aspirator that does not create a chocking hazard and that generates greater suction.

Nasal aspirators have been used particularly with young children to create a partial vacuum for suctioning nasal discharge from the child's nostril. A typical nasal aspirator includes an oval shaped bulb, a tip, and a stem. The bulb is generally made out of a rubber type of material that has an opening into an inner hollow cavity. The tip is secured to the stem which extends into the inner hollow cavity through the opening in the bulb. The tip is generally glued to the stem and has a total length from a bottom of the stem to a point of the tip of approximately one inch. The tip typically extends approximately one half inch above the opening of the bulb so that the stem typically extends approximately one half inch into the inner cavity of the bulb.

The nasal aspirator is used by compressing the bulb which forces air out of the inner hollow cavity through an opening in the tip. The tip is then placed and aligned with the nasal passage of the child so as co create a seal between the tip and the nasal passage. Once in place, the compressed bulb is then released creating a temporary vacuum due to the pressure within the inner hollow cavity of the bulb being less than the pressure of the external environment. The pressure differential creates a partial vacuum causing a suction at the opening of the tip. The suction at the opening of the tip directs discharge within the nasal passage into the nasal aspirator. The nasal aspirator thus assists in cleaning and clearing the child's nasal passage.

The tip and the stem used with current nasal aspirators can be easily removed from the opening in the bulb. Once removed, the tip and the stem can become a choking hazard. Current nasal aspirators fail to meet the Toy Standards established by the Consumer Product Safety Commission, which require all parts of a device to conform to certain width and length restrictions to avoid choking hazards. Currently available nasal aspirators fail the standards due to their shorter tip and stem constructions.

The tip in known nasal aspirators is also glued to the stem that is inserted into the bulb. As a result of use and cleaning, the glued connection between the tip and the stem may loosen or fail causing the tip to separate from the stem and create an even greater choking hazard by the smaller individual component parts.

Current nasal aspirators also have a flat edge along their opening in the bulb that the stem is inserted through. The flat edge around the opening of the bulb tends to cause a loss of volume and pressure when the bulb is compressed and is used as a vacuum to suction discharge from the nasal passage. The loss of pressure is a result of air entering around the gaps formed between the flat edge opening of the bulb and the stem. These air gaps decrease the suction through the opening of the tip as the vacuum within the inner hollow cavity is neutralized.

The shorter length of the tip and the stern for known nasal aspirators also tends to cause discharge suctioned from the nasal passage to pass through the tip and stem and be deposited within the inner hollow cavity of the bulb. The opening in the bulb into the inner hollow cavity is typically only around a half an inch in diameter making it difficult to properly clean the inner hollow cavity of the bulb. However, with nasal discharge contained within the inner hollow cavity, continuous proper cleaning would be required to maintain the inner hollow cavity in a sanitary condition and avoid the spread of germs or undesirable biological growth.

There is no known nasal aspirator which is inviting to children, does not present a choking hazard, and generates greater suction.

BRIEF SUMMARY OF THE INVENTION

The invention is a device and method for an improved nasal aspirator that is inviting to children and provides increased suction without creating a choking hazard. The nasal aspirator comprises a stem, a tip, and a bulb. The stem has an inner lumen from a bottom to a top and an outward radial flange that extends from the top of the stem to create a mounting surface. The tip includes a point that arches from a base and has an aperture at the point. The base of the tip is secured to the top of the stem at the mounting surface by an adhesive and then is ultrasonically welded together to improve the strength of the connection. The bulb creates an inner hollow cavity that is accessed by an opening. The opening of the bulb includes a series of ribs that the bottom of the stem is inserted into until the top of the stem is secured at the opening of the bulb. The stem has a length which is greater than the height of the tip so that the stem extends further into the inner hollow cavity of the bulb capturing the nasal discharge within the lumen rather than having it deposited along the inner wall of the bulb. The greater length of the stem also prevents the stem and the tip from becoming a choking hazard.

BRIEF DESCRIPTION OF THE DRAWINGS

FIG. 1 is a perspective view of a preferred embodiment of the invention.

FIG. 2 is an exploded, sectional view of a preferred embodiment of the invention.

DETAILED DESCRIPTION

FIG. 1 is a perspective view of a preferred embodiment of the nasal aspirator 10. The nasal aspirator 10 includes a bulb 12, a stem 14 (shown in phantom), and a tip 16. The bulb 12 has an opening 18 (shown in phantom) that the stem 14 is inserted into. The tip 16 is secured to the stem 14. The nasal aspirator 10 is used to suction discharge from a nasal passage, typically of a child. In a preferred embodiment, the bulb 12 of the nasal aspirator 10 has a shape of an animal to help overcome a child's fear of the device by introducing features to the child which are familiar and inviting. As shown in FIG. 1, the bulb 12 can be formed in the shape of a teddy bear. The teddy bear shape of the bulb 12 may help the child associate positively with the device and avoid creating anxiety in the child or causing the child to resist use of the device.

FIG. 2 is an exploded, sectional view along section 2—2 of FIG. 1. As shown in FIG. 2, the bulb 12 further includes a series of ribs 20 placed along the opening 18. The opening 18 accesses an inner hollow cavity 22 of the bulb 12. In a preferred embodiment, the bulb 12 is made from a non-latex, polymeric material, such as polyvinyl chloride. A plasticizer is preferably added to the polyvinyl chloride to achieve a quick response from compressing and then releasing the bulb 12. The bulb 12 preferably does not include latex in its material make-up to avoid a potential allergic reaction from use or handling of the bulb 12. The bulb 12 is formed with a skin thickness of approximately 1.5 millimeters. If the bulb 12 is formed in the shape of an animal, then the non-latex, polymeric material is preferably dyed or painted to match the color of the animal. As shown in the present embodiment, the bulb 12 would preferably be dyed brown to match the teddy bear shape of the bulb 12.

The series of ribs 20 are preferably placed around the opening 18 to improve the seal between the bulb 12 and the stem 14. This is especially important when a vacuum condition is created with the nasal aspirator 10, such as after the bulb 12 has been compressed and the tip 16 has been sealed against a nasal passage. The improved seal between the bulb 12 and the stem 14 at the opening 18 helps avoid loss of vacuum from within the inner hollow cavity 22 by air entering into the inner hollow cavity 22 from between the bulb 12 and the stem 14 at the opening 18.

The stem 14 preferably includes an inner lumen 24 that extends from a bottom 26 to a top 28. A flange 30 extends radially outward to create a mounting surface for the tip 16 at the top 28 of the stem 14. The flange 30 further includes an upright member or ring 32 that extends annularly from the flange 30 at a side and in a direction opposite the top 28 of the stem 14. The upright member 32 provides a guide for properly placing the tip 16 onto the mounting surface created by the flange 30 of the stem 14.

The tip 16 includes an aperture 34 at a point 36 that arches from a base 38. The base 38 includes a radial body 40 that mates with and is secured to the mounting platform of the flange 30. The upright member 32 also assists in positioning the radial body 40 for proper placement of the base 38 onto the flange 30. The upright member 32 contacts an inside surface 42 of the tip 16 along the base 38. When properly aligned, the aperture 34 is aligned with the lumen 24 of the stem 14. The stem 14 and the tip 16 are preferably made from clear plastic that may be tinted to match the characteristics of a hat for the animal shape of the bulb 12. Whether the stem 14 and the tip 16 are clear or tinted, the inner lumen 24 or inside surface 42 remain observable through the stem 14 or the tip 16 to ensure that they are properly cleaned and to monitor the performance of the aspirator 10.

In a preferred embodiment, the combination of the stem 14 and the tip 16 create an overall length of at least 2 inches to avoid creating a choking hazard as set forth by the Toy Standards of the Consumer Product Safety Commission. To meet the minimum length requirements and to avoid having the tip 16 extend an excessive distance beyond the opening 18 in the bulb 12, the stem 14 preferably extends into the bulb 12 a greater distance than the tip 16 extends above the bulb 12. In a preferred embodiment, the stem 14 has a length of approximately 48.7 millimeters, an outer diameter of approximately 8.6 millimeters, and an inner diameter of approximately 5.0 millimeters at the bottom 26. At the top 28, the flange 30 preferably has an outer diameter of approximately 19.8 millimeters. The upright member 32 preferably extends in an annular direction above the flange 30 approximately 1.5 millimeters with an inner diameter of approximately 11.3 millimeters and an outer diameter of approximately 14.3 millimeters.

The radial body 40 of the tip 16 preferably extends beyond the flange 30 and thus has an outer diameter of approximately 25.2 millimeters. The tip 16 preferably has a height of approximately 17.8 millimeters from the base 38 to the point 36 and the aperture 34 has a diameter of approximately 2.8 millimeters.

The tip 16 is preferably secured to the stem 14 by an adhesive between the radial body 40 and the flange 30. After the tip 16 is initially adhered to the stem 14, the radial body 40 of the tip 16 is then ultrasonically welded to the flange 30 of the stem 14. By ultrasonically welding the connection between the tip 16 and the stem 14, in addition to use of the adhesive, a much more secure connection is made between the tip 16 and the stem 14.

The stem 14 is inserted further into the inner hollow cavity 22 of the bulb 12 as compared to current aspirators due to its longer length. The greater length of the stem 14 prevents the combination of the tip 16 secured to the stem 14 from becoming a choking hazard and helps prevent nasal passage discharge from being suctioned into the inner hollow cavity 22 of the bulb 12. By the longer length of the stem 14, the discharge is captured in the lumen 24 rather than in the cavity 22. The nasal aspirator 10 can then be cleaned by simply removing the stem 14 from the opening 18 in the bulb 12 and washing the stem 14 and the tip 16.

A nasal aspirator in the shape of an animal is more likely to be inviting and well received by a child due to the child's association with the familiar features incorporated into its design. Additionally, the current nasal aspirator does not create a choking hazard even when the tip and stem are removed from the bulb. Ultrasonically welding the tip to the stem, in addition to using adhesive, makes it much less likely that the tip would separate from the stem and become a choking hazard. The longer length of the stem, in addition to avoiding a choking hazard, improves the serviceability of the nasal aspirator by making it easier to clean. Nasal discharge from use of the aspirator is more likely to remain within the longer length of the stem, which is easier to clean, rather than being deposited along the inner surface of the bulb in the inner hollow cavity. The bulb also provides a ribbed opening to improve the seal formed between the bulb and the stem and thus increases the suction capability of the aspirator.

Although the present invention has been described with reference to preferred embodiments, workers skilled in the art will recognize that changes may be made in form and detail without departing from the spirit and scope of the invention. For example, the bulb can be formed as a different animal, such as a dog, or as some other familiar object, such as a car or a block. Further, the dimensions of the aspirator or its components could also be altered.

What is claimed is:

1. A nasal aspirator comprising:

a stem having an inner lumen from a top to a bottom of the stem;

a tip having a base and a top, wherein the top has an aperture and the base is secured to the top of the stem, and a bulb having a shape similar to an animal including a head and a body, the bulb having a ribbed opening located at the lead of the animal and extending within an inner hollow cavity, wherein the stem is inserted through the ribbed opening such that the bottom of the stem extends into the inner hollow cavity and the top of the stem is secured at the ribbed opening of the bulb so that the stem and the tip create an appearance of a hat.

2. The nasal aspirator of claim 1, wherein the stem extends into the inner hollow cavity of the bulb a greater distance than the tip extends above the opening of the bulb.

3. The nasal aspirator of claim 1, wherein a flange extends radially outward at the top of the stem to create a mounting platform to which the base of the tip is secured.

4. The nasal aspirator of claim 3, wherein an upright member extends annularly from the flange to contact an inner surface of the tip along the base to assist in guiding proper placement of the tip on the stem.

5. The nasal aspirator of claim 1, wherein the tip is secured to the stem by an adhesive compound and is ultrasonically welded.

6. A nasal aspirator comprising:
- a bulb having an opening into an inner hollow cavity, the bulb having a shape of an animal including a head and a body;
- a stem having an inner lumen from a top to a bottom, the bottom of the stem extending into the inner hollow cavity through the opening;
- a tip having a base and a top, wherein the top has an aperture and the base is secured to the top of the stem which extends out of the opening of the bulb; and
- a flange extending radially outward at the top of the stem such that the flange sits atop the head of the animal shaped bulb creating an appearance of a hat when the base of the tip is mounted to the flange.

7. The nasal aspirator of claim 6, wherein the opening at the bulb is ribbed.

8. The nasal aspirator of claim 6, wherein the stem has a length of approximately 48.7 millimeters.

9. The nasal aspirator of claim 6, wherein an upright member extends annularly from the flange to contact an inner surface of the tip along the base to assist in guiding the proper placement of the tip on the stem.

10. The nasal aspirator of claim 6, wherein the tip is secured to the stem by an adhesive compound and is ultrasonically welded.

11. A nasal aspirator comprising:
- a bulb having a shape similar to an animal including a head and a body, the bulb having an opening into an inner hollow cavity;
- a stem that is secured by the opening of the bulb, the stem having an inner lumen from a bottom that extends into the inner hollow cavity to a top that extends out of the opening of the bulb;
- a tip having a base secured to the top for the stem, the base arching to a point that has an aperture;
- a flange extending radially outward at the top of the stem such that the flange rests atop the head of the animal shaped bulb to create a mounting platform to which the base of the tip can be secured; and
- an upright member extending annularly from the flange to contact an inner surface of the tip along the base to assist in guiding proper placement of the tip on the stem.

12. The nasal aspirator of claim 11, wherein the opening at the bulb is ribbed.

13. The nasal aspirator of claim 11, wherein the stem has a length of approximately 48.7 millimeters.

* * * * *

UNITED STATES PATENT AND TRADEMARK OFFICE
CERTIFICATE OF CORRECTION

PATENT NO. : 6,290,667 B1
DATED : September 18, 2001
INVENTOR(S) : Daniel G. Cook It is certified that error appears in the above-identified patent and that said Letters Patent is hereby corrected as shown below:

<u>Column 4,</u>
Line 52, delete "lead", insert -- head --

Signed and Sealed this

Fourth Day of June, 2002

*Attest:*

JAMES E. ROGAN
*Attesting Officer*     *Director of the United States Patent and Trademark Office*